United States Patent
Tucker-Schwartz et al.

(10) Patent No.: US 9,772,282 B2
(45) Date of Patent: Sep. 26, 2017

(54) SYSTEM FOR WIDE FIELD-OF-VIEW, HIGHLY OBLIQUE ILLUMINATION MICROSCOPY FOR SCATTER-BASED DISCRIMINATION OF CELLS

(71) Applicant: Massachusetts Institute of Technology, Cambridge, MA (US)

(72) Inventors: Jason Michael Tucker-Schwartz, Cambridge, MA (US); Shivang Rajendra Dave, Boston, MA (US); German Gonzalez Serrano, Alicante (ES)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/213,870

(22) Filed: Jul. 19, 2016

(65) Prior Publication Data
US 2017/0138849 A1 May 18, 2017

Related U.S. Application Data

(60) Provisional application No. 62/254,266, filed on Nov. 12, 2015, provisional application No. 62/341,141, filed on May 25, 2016.

(51) Int. Cl.
*G01N 21/00* (2006.01)
*G01N 21/49* (2006.01)
(Continued)

(52) U.S. Cl.
CPC ......... *G01N 21/49* (2013.01); *G01N 15/0211* (2013.01); *G01N 15/1429* (2013.01);
(Continued)

(58) Field of Classification Search
CPC ......... G01N 21/6486; G01N 2201/061; G01N 2458/00; G01N 27/447; G01N 27/44756;
(Continued)

(56) References Cited

U.S. PATENT DOCUMENTS

| 5,907,398 A | * | 5/1999 | Fujino | ............... G01N 21/8806 257/E21.53 |
| 7,595,874 B1 | * | 9/2009 | Pelekhaty | .......... G01N 21/6458 356/318 |

(Continued)

OTHER PUBLICATIONS

Shapiro; ""Cellular astronomy"—a foreseeable future in cytometry,"; Cytometry Part A: The Journal of the International Society for Analytical Cytology: Aug. 2004; pp. 115-124; vol. 60A, Issue 2; International Society for Advancement of Cytometry; USA.

(Continued)

*Primary Examiner* — Michael P Stafira
(74) *Attorney, Agent, or Firm* — Sam Pasternack; MIT Technology Licensing Office (57) ABSTRACT

System for scatter-based differentiation of cells. The system includes a planar substrate having cells disposed thereon for imaging and a microscope employing relatively low magnification detection optics providing a wide field of view focused on the cells on the substrate and defining a microscope optical axis. An illuminator delivers light to the ceils on the substrate focused to a spot larger than the field of view of the microscope, the illuminator having an illumination optical axis highly oblique to the microscope optical axis wherein scattered light is collected by the microscope. A defection system receives the scattered light from the microscope to provide a measure of signal intensity and a measure of size for each cell for discrimination of cell type.

22 Claims, 6 Drawing Sheets

(51) Int. Cl.
- G01N 15/02 (2006.01)
- G01N 15/14 (2006.01)
- G01N 21/64 (2006.01)
- G01N 33/483 (2006.01)
- G02B 21/34 (2006.01)
- G02B 21/16 (2006.01)
- G02B 21/10 (2006.01)
- G01N 15/00 (2006.01)
- G01N 15/10 (2006.01)

(52) U.S. Cl.
CPC ..... *G01N 15/1434* (2013.01); *G01N 15/1463* (2013.01); *G01N 21/6458* (2013.01); *G01N 21/6486* (2013.01); *G01N 33/483* (2013.01); *G02B 21/10* (2013.01); *G02B 21/16* (2013.01); *G02B 21/34* (2013.01); *G01N 2015/008* (2013.01); *G01N 2015/0073* (2013.01); *G01N 2015/1006* (2013.01); *G01N 2015/1081* (2013.01); *G01N 2201/062* (2013.01); *G01N 2201/12* (2013.01)

(58) Field of Classification Search
CPC ............. G01N 33/487; G01N 33/5091; G01N 21/9501; G01N 21/6458; G01N 2021/8867; G01N 21/88; G01N 21/956; G01N 21/6452

See application file for complete search history.

(56) References Cited

U.S. PATENT DOCUMENTS

| | | | |
|---|---|---|---|
| 2005/0121604 A1* | 6/2005 | Mueth | A61M 1/36 250/251 |
| 2007/0229801 A1* | 10/2007 | Tearney | A61B 5/0062 356/73 |
| 2008/0212069 A1* | 9/2008 | Goldberg | B01L 3/502761 356/36 |
| 2009/0032449 A1* | 2/2009 | Mueth | G02B 21/32 210/94 |
| 2009/0086314 A1* | 4/2009 | Namba | G01N 21/6458 359/383 |
| 2012/0206727 A1* | 8/2012 | Schulte | G01J 3/0289 356/402 |
| 2012/0257196 A1* | 10/2012 | Raicu | G02B 21/002 356/300 |
| 2012/0310538 A1* | 12/2012 | Stewart | G06K 9/00127 702/19 |
| 2016/0216208 A1* | 7/2016 | Kim | G01N 21/6452 |

OTHER PUBLICATIONS

Shapiro; "The Cytometric Future: It Ain't Necessarily Flow!,"; Flow Cytometry Protocols; Nov. 15, 2010; pp. 471-482; vol. 699: Humana Press, USA.

Shapiro; "Personal cytometers: Slow flow or no flow?,"; Cytometry Part A: May 2006; pp. 620-630; vol. 69A, Issue 7: International Society for Advancement of Cytometry; USA.

Shapiro; "Killer applications: Toward affordable rapid cell-based diagnostics for malaria and tuberculosis,": Cytometry Part B: Clinical Cytometry; Jan. 2008; pp. S152-S164; vol. 74B, Clinical Cytometry Society; USA.

Wittrup; "Fluorescence Array Detector for Large-Field Quantitative Fluorescence Cytometry,"; Cytometry Part A; Jul. 1994; pp. 206-213: vol. 16, Issue 3; International Society for Advancement of Cytometry: USA.

Mullaney; "Cell Sizing—a Light Scattering Photometer for Rapid Volume Determination,"; Review of Scientific Instruments; 1969: pp. 1029-1032; vol. 40; AIP Publishing; USA.

Price; "Light-Scatter Analysis of Microalgae—Correlation of Scatter Patterns from Pure and Mixed Asynchronous Cultures,"; Biophysical Journal; Apr. 1978; pp. 29-36; vol. 22, issue 1; the Biophysical Society; USA.

Sklar; , "Neutrophil degranulation detected by right angle light scattering: spectroscopic methods suitable for simultaneous analyses of degranulation or shape change, elastase release, and cell aggregation,"; Journal of Immunology; Sep. 1, 1984; pp. 1483-1487; vol. 122, No. 3; American Association of Immunologists; USA.

McNeil; "Light-Scattering Changes during Chemotactic Stimulation of Human-Neutrophils—Kinetics Followed by Flow-Cytometry,"; Cytometry Part A; Jan. 1985; pp. 7-12; vol. 6, Issue 1; International Society for Advancement of Cytometry; USA.

Benson; , "The Application of Perpendicular and Forward Light Scatter to Assess Nuclear and Celluar Morphology,"; Cytometry Part A; Sep. 1984; pp. 515-522; vol. 5, Issue 5; International Society for Advancement of Cytometry; USA.

McGann; "Light-Scattering and Cell Volumes in Osmotically Stressed and Frozen-Thawed Cells,"; Cytometry Part A; Jan. 1988; pp. 33-38; vol. 9, Issue 1; International Society for Advancement of Cytometry; USA.

Yyguerabide: "Light-scattering submicroscopic particles as highiy fluorescent analogs and their use as tracer labels in clinical and biological applications,"; Analytical Biochemistry; Sep. 10, 1998; pp. 157-176; vol. 262, Issue 2: Academic Press; USA.

Watson; "Elastic light scattering from single cells: orientational dynamics in optical trap,"; Biophysical Journal; Aug. 2004; pp. 1298-1306; vol. 87, Issue 2; Cell Press; USA.

Smal; "Quantitative comparison of spot detection methods in fluorescence microscopy,"; IEEE Transactions on Medical Imaging; Jun. 23, 2009; pp. 282-301; vol. 29, Issue 2; IEEE; USA.

Herbert; "FindFoci: a focus detection algorithm with automated parameter training that closely matches human assignments, reduces human inconsistencies and increases speed of analysis,"; PloS One; Dec. 5, 2014; San Francisco, CA.

Cunliffe; "An approach to the validation of flow cytometry methods,"; Pharmaceutical Research; Oct. 14, 2009; pp. 2551-2557; vol. 26; Springer US; USA.

Owens; "Validation and quality control of immunophenotyping in clinical flow cytometry,"; Journal of Immunological Methods; Sep. 21, 2000; pp. 33-50; vol. 243; Issues 1-2; Elsevier; USA.

Nicholson; "Use of CD45 fluorescence and side-scatter characteristics for gating lymphocytes when using the whole blood lysis procedure and flow cytometry,"; Cytometry Part A; Mar. 15, 1996; pp. 16-21; vol. 26, Issue 1: Internetional Society for Advancement of Cytometry; USA.

Wei; , "A machine vision system for automated non-invasive assessment of cell viability via dark field microscopy, wavelet feature selection and classification,"; BMC Bioinformatics; Oct. 21, 2008; vol. 9; BioMed Central; USA.

Ciurte; , "Circulating tumor cells classification and characterization in dark field microscopic images of unstained blood,"; 2016 IEEE International Conference on Intelligent Computer Communication and Processing (ICCP): pp. 367-374; IEEE; USA.

Wei; "An in situ probe for on-line monitoring of cell density and viability on the basis of dark field microscopy in conjunction with image processing and supervised machine learning,"; Biotechnology and Bioengineering; Feb. 1, 2007; pp. 1489-1500; Wiley Periodicals, Inc; USA.

Johnson; , "Optical light scatter imaging of cellular and sub-cellular morphology changes in stressed rat hippocampal slices,"; Journal of Neuroscience Methods; May 15, 2000; pp. 21-31; vol. 98, Issue 1; Elsevier; USA.

Landry; "Oblique incidence reflection imaging of live cells: improving contrast and image quality with an objective mask,"; Journal of Microscopy: Aug. 2007; pp. 185-189; vol. 227, Issue 2; the Royal Microscopical Society; Oxford, UK.

Landry; "Monitoring live cell viability: Comparative study of fluorescence, oblique incidence reflection and phase contrast microscopy imaging techniques,"; Optics Express; 2004, pp. 5754-5759; vol. 12, Issue 23; OSA Publishing; USA.

(56) References Cited

OTHER PUBLICATIONS

Kawano; "Darkfield Adapter for Whole Slide Imaging: Adapting a Darkfield Internal Reflection Illumination System to Extend WSI Applications,"; PloS One; Mar. 8, 2013; pp. 1-12; vol. 8, Issue 3: San Francisco, CA.

Yguerabide: "Resonance light scattering particles as ultrasensitive labels for detection of analytes in a wide range of applications,"; Journal of Cellular Biochemistry; 2001; pp. 71-81; vol. 84; Wiley Periodicals, Inc.; USA.

Bundscherer; "Cell harvesting method influences results of apoptosis analysis by annexin V staining,"; Anticancer Research; Aug. 2013; pp. 3201-3204; vol. 33, No. 8: USA.

Sharpless; "Size and Refractive-Index Dependence of Simple Forward Angle Scattering Measurements in a Flow System Using Sharply-Focused Illumination,"; Journal of Histochemistry and Cytochemistry; Jan. 25, 1977: pp. 845-856; vol. 25, No. 7; the Histochemical Society, Inc.; USA.

Salzman; "Light-scatter: detection and usage,"; Current Protocols in Cytometry; 2001; pp. 1.13.1-1.13.8; John Wiley and Sons, Inc.; USA.

\* cited by examiner

SYSTEM FOR WIDE FIELD-OF-VIEW, HIGHLY OBLIQUE ILLUMINATION MICROSCOPY FOR SCATTER-BASED DISCRIMINATION OF CELLS

This application claims priority to provisional application Ser. No. 62/254,266 filed on Nov. 12, 2015 and also claims priority to provisional application Ser. No. 62/341,141 filed on May 25, 2016. The contents of both of these provisional applications are incorporated herein by reference in their entirety.

BACKGROUND OF THE INVENTION

Cellular astronomy is a microscopy-based approach to cytometry that uses low magnification, wide field-of-view imaging of stationary cell samples and phenotypic markers borrowed from flow cytometry to enumerate different cell subpopulations [1-4]. By leveraging the simplicity of low resolution microscopy, many cells can be imaged simultaneously over a large field-of-view while being treated similar to point sources, analogous to flow cytometry [1-3, 5]. With cell astronomy, shifting the cellular analysis paradigm towards low-magnification microscopy holds the potential to lower technology barriers to acquiring high throughput cytometry data in the life science research setting due to the prevalence of fluorescence microscopy systems. The use of cell astronomy could allow for more wide-scale deployment of flow cytometry measurements to those labs that possess fluorescence microscopes but do not possess dedicated flow cytometry instrumentation.

To date, cellular astronomy has used fluorescence labels alone to identify and distinguish cell types [2-4]. There would be significant value in additionally measuring the elastic light scattering parameters inherent to flow cytometry with a cellular astronomy system. In flow cytometry, elastic scattering is used to approximate relative cell size (by low angle forward scattered light) and internal cell complexity (by wide-angle side-scattered light) [6, 7]. These forward and side-scattering measures allow for grouping of cell subtypes in a label-free manner (i.e., without fluorescent labeling) [8-14], avoiding unnecessary sacrifice of the optical wavelength spectrum so that more informative molecular biomarkers can be labeled for fluorescence detection. Maintaining the available fluorescent bandwidth by utilizing scatter-based measurements is especially advantageous for microscopy-based cytometry measurements, as many existing fluorescent microscopes are designed to acquire data from a limited number of fluorescence channels. The ability to mimic these forward and side scatter measurements could further unlock wide field-of-view, low resolution microscopy as a potential alternative for gathering high throughput cytometry data.

An object of the invention is a label-free, wide-field scatter-based imaging modality that collects forward and side scatter surrogate data at low-magnification using highly oblique illumination microscopy (HOIM), effectively demonstrating the scatter measurement capabilities of the cellular astronomy approach disclosed herein.

A further object of the invention is image processing algorithms that estimate size and signal intensity from HOIM images of white blood cells.

SUMMARY OF THE INVENTION

In one aspect, the invention is a system for scatter-based differentiation of cells. The cells may be stationary or flowing. The system includes a planar substrate having cells disposed thereon for imaging. A microscope is provided employing relatively low magnification detection optics providing a wide field of view focused on the cells on the substrate and defining a microscope optical axis. An illuminator is provided for delivering light to the cells on the substrate focused to a spot larger than the field of view of the microscope, the illuminator having an illumination optical axis highly oblique to the microscope optical axis wherein scattered light is collected by the microscope. A detection system receives the scattered light from the microscope to provide a measure of signal intensity (side scatter) and a measure of size (forward scatter surrogate) for each cell for discrimination of cell type. In a preferred embodiment of the invention the cells are white blood cells. Microscope magnification may be in the approximate range of 0.2 to 4×. A suitable low magnification for the microscope is approximately 4×.

In a preferred embodiment, the illuminator includes a 455 nm center wavelength, light emitting diode. The highly oblique angle is at least 50 degrees in relation to the normal to the sample surface and a preferred angle is 82 degrees. In this embodiment the detection system includes algorithms to measure size and signal intensity from each cell.

DESCRIPTION OF THE PREFERRED EMBODIMENT

Figure 1:
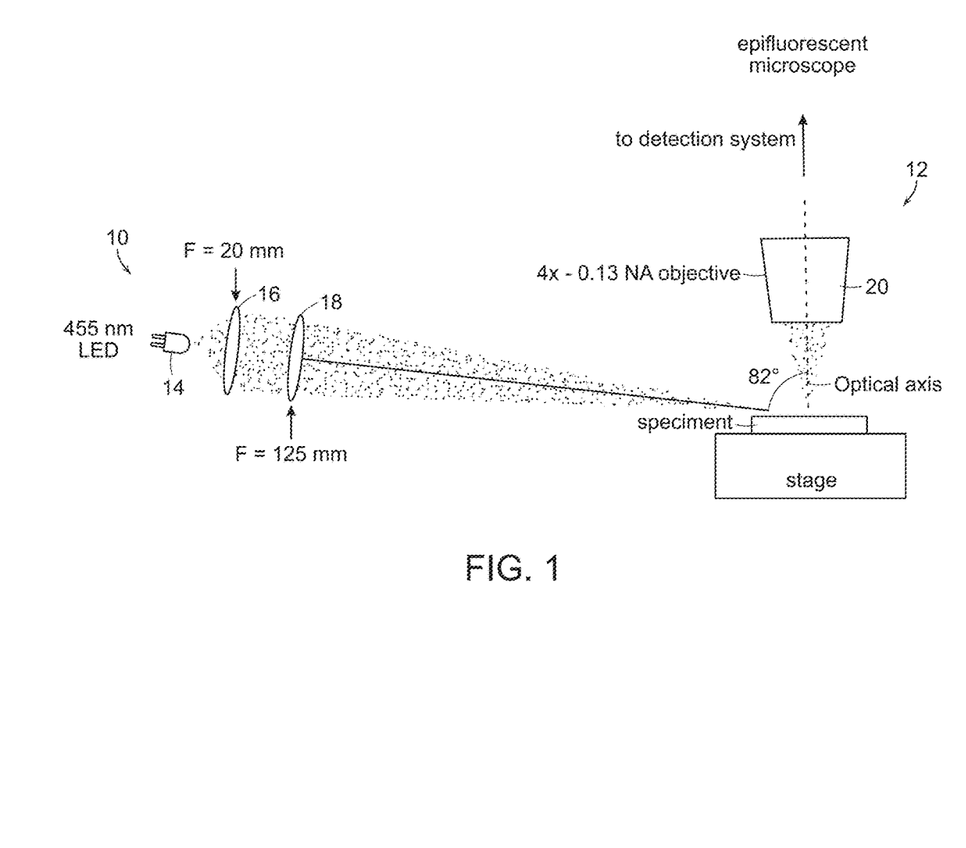
FIG. 1 is a schematic illustration of the highly-oblique illumination microscopy (HOIM) system disclosed herein.

With reference to FIG. 1, a custom HOIM illuminator 10 that allows for homogenous side scatter data collection over a wide field-of-view was positioned alongside a commercial clinical observation microscope 12 (CX41, Olympus) with epi-illumination fluorescence capabilities. This approach is similar to those proposed for high resolution dark field microscopy of nanoparticles [15]. A high power 455 nm center wavelength LED 14 (M455L3, Thorlabs) served as the illumination source. The light diverging from the LED 14 was collected by an aspheric lens (F=20 mm) 16 located approximately one focal length away from the LED 14. A folly open aperture stop was used to remove spurious light from the illuminator 10. A bi-convex lens (F=125 mm) 18 re-focused the LED 14 light to a spot larger than the field-of-view of the commercial microscope 12, allowing for increased irradiance when compared to the collected but unfocused LED light. The illuminator 10 was placed approximately 125 mm away from the focal plane of the commercial microscope, and tilted 82 degrees from the optical detection path. Slightly offsetting the collection lens-to-LED distance from one lens focal length allowed for slight blurring of the LED structure that would otherwise cause illumination inhomogeneities over the field-of-view. This setup allows the existing microscope optics to act as the detection pathway for light that has been scattered at a highly oblique angle relative to the illuminator 10. This set of scatter angles is a subset of the side scatter angles captured by standard flow cytometry instrumentation [7], and falls within a range that allows for significant separation between white blood cell groups [16]. The highly oblique illumination angle (82 degrees, for example) results in surface reflection losses (>40%) away from the surface of the sample. Although this reduced the strength of signal, the reflected light was not captured by the optics, did not contaminate the image signal, and was easily accommodated by increased image acquisition time. Suitable highly oblique angles are in the range 90° to 60°, 85° to 65°, 85° to 70° or 75° to 85°. More generally, the highly oblique angle minimizes collection of reflected light and maximizes the collection of side scattered light.

HOIM images were acquired using the custom illuminator 10 and commercial microscope 12 for detection. The microscope 12 included a 4×0.13 NA fluorite imaging objective 20 (UPLFLN4X, Olympus), and a 4 megapixel, 7.4 μm pixel monochrome CCD (FX1500, SPOT Imaging). With the 4× objective 20, the field-of-view of the camera was approximately 3.8×3.8 mm (14.44 mm2 imaging area). An epi-fluorescence illuminator (CX-RFA-2, Olympus) allowed for fluorescence measurements of cells labeled with Alex a Fluor 532 antibody conjugates. A 520 nm center wavelength high power LED (UHP-Mic-LED-520, Prizmatix) was used for fluorescence illumination. A wide band green filter cube (CX-DMG-2, Olympus) containing a bandpass excitation filter centered at 515 nm, dichroic mirror with transition at 570 nm, and a 590 nm longpass emission filter were used for fluorescence measurements. For fluorescence measurements, the integration time of the CCD was set to 5 seconds. To increase SNR, two sequential fluorescence images were taken for each field-of-view and then averaged. For HOIM measurements, the filter cube was removed from the optical path, and a single image was acquired at an integration time of 50 ms.

Figure 2A:
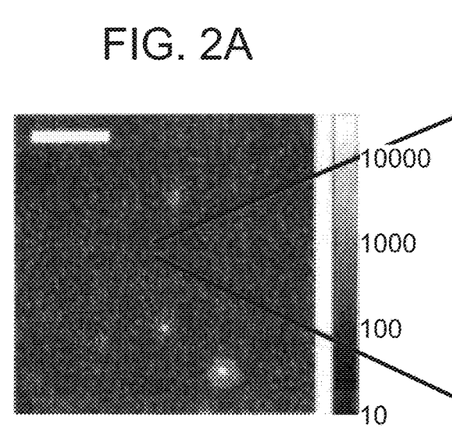
FIG. 2a is an image showing raw 4× HOIM images of granulocytes with a log-scale color bar.

HOIM images were analyzed using a custom algorithm to measure the approximate size and signal intensity from each cell in the image, serving as surrogates of forward and side scatter flow cytometry measurements, respectively. An automated algorithm used to analyze cells in the HOIM images (FIG. 2a) was separated into two ordered steps; event detection (FIG. 2b) followed by cell signal estimation (FIG. 2c).

Figure 2B:
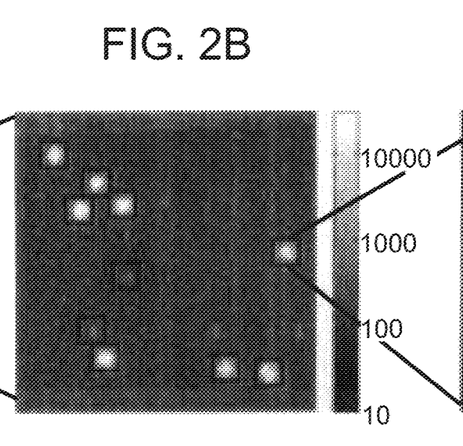
FIG. 2b is a digitally zoomed image region showing low magnification microscopy images of cells.
Figure 2C:
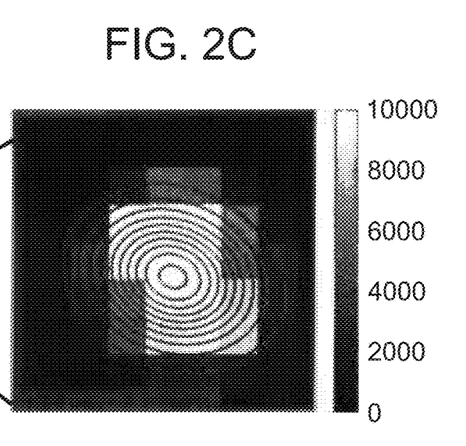
FIG. 2c is a subset image region selected around each cell and it by a 2D Gaussian.

Event detection, identified all cell-like image features from the HOIM image for further analysis (blue boxes, FIG. 2b). The event detection is based on a sliding window approach that classifies every patch as containing or not containing a cell. The chosen event detection classifier is a linear discriminant analysis (LDA) algorithm, which has been shown to achieve high performance even on low SNR images [17]. The first step is training of the classifier that calculates the adequate parameters to enable classification of events in new images. For the training step, we acquired co-registered HOIM and fluorescence images of blood cell samples labeled with Alexa Fluor 532 anti-CD45, used to positively identify white blood cells (and avoid cell and other debris) in the field-of-view. CD45 fluorescence images were background subtracted using a top hat filter with a 5 pixel radius kernel, then median filtered over a 3 by 3 pixel neighborhood. Ground truth locations of white blood cells in the CD45 fluorescence image were calculated in ImageJ using the Find Foci function [18]. At the coordinate locations found using the CD45 fluorescence images, a 9 by 9 pixel patch was extracted around every cell in the co-registered HOIM image, with the pixels serving as LDA features. From 4 training images, 6,726 image patches were used to train the classifier. For classification of a new image, a patch of 9 by 9 pixels was extracted around every image pixel and its intensity was normalized between zero and one. The LDA model was applied to the resulting vector, creating a probabilistic value for that pixel that a cell was centered at that point in the image. The probabilistic output image from the LDA model was then thresholded at a probability of 99.9%, creating a binary map showing coordinate locations where the algorithm identified each cell.

After identifying the location of cell signals, each signal was analyzed to extract surrogate forward and side-scatter parameters. A 9 by 9 pixel region (i.e. image patch) around every cell location was separately analyzed, and the data in the patch was fit to a mixture model containing a uniform distribution and a Gaussian distribution. The background is described by a uniform distribution, while the Gaussian describes the cell intensity. This Gaussian assumption holds well for low resolution images where distinct cellular morphology features are no longer clearly visible. The fit optimization was carried out using an expectation maximization (EM) technique [19, 20], Once the algorithm converged, the posterior probability of the Gaussian distribution was computed for each pixel in the image patch and multiplied by image pixel intensity; the HOIM signal intensity was obtained by integrating all pixel values in the patch after the multiplication step. Multiplying the probability map with the pixels in the image patch ensured removal of background scatter. This measurement served as a surrogate to the side scatter measurements commonly obtained with flow cytometry. The size of the cell (the surrogate for flow cytometry forward scatter) was estimated by computing the area of the bounding box containing the cell.

Taking advantage of the Gaussian fit, we assume the Gaussian shape span is 3σ in each of the two main orientations. Thus the total area can be computed by multiplying the two eigenvalues of the Gaussian fit covariance matrix. To avoid the impact of doublet events (i.e. touching cells) on data analysis, samples with any eigenvalue greater than a predetermined threshold were eliminated from analysis. This is the HOIM analog to how cytometer forward scatter metrics used to eliminate double events from further analysis. This novel method of image analysis is necessary to accurately estimate size and cell brightness in low magnification images where partial volume effects, low signal-to-noise ratio, and background signal can create errors in analysis [20]. The algorithm requires cell signals to approximate a Gaussian distribution, which held true for the magnification and pixel size used here. At some point of demagnification, we expect the algorithm to no longer distinguish cell types. Although the theoretical and practical limit of this has not been evaluated, we have found qualitatively similar performances at 2× and 4× magnification.

Positive procedural controls for immunophenotyping, CD-Chex Plus (Lots 5250 and 5306, Streck), were used for imaging studies, a control sample manufactured from normal human leukocytes and erythrocytes widely adopted for quality control of flow cytometry systems [21, 22]. These samples have validated control data for a number of cell differentiation biomarkers, and most importantly, mimic forward and side scatter of human blood cells. Since there are no well validated control samples (i.e., beads) that recreate variation in scatter between cell types that the inventors are aware of commercially available, well-validated control cell samples were used to assess the illumination and image analysis capabilities of the system.

CD-Chex samples with varying percentages of the three major white blood cell populations (lymphocytes, monocytes, granulocytes) were used for characterization of the HOIM system. All samples were labeled with fluorescent human anti-CD45 antibodies and underwent red blood cell lysis using standard protocols from reagent manufacturers as a guideline. First, all reagents including the CD-Chex samples were allowed to reach room temperature. To positively identify white blood cells in the field-of-view, 500 µL of CD-Chex was added to 25 µL (0.3 µg) of Alexa Fluor 532-labeled anti-CD45 antibodies (eBiscienee), and allowed to react for 25 minutes at room temperature while protected from light. After antibody incubation, 5 mL of 1× red blood cell lysis buffer (eBioscience) was added to the sample and mixed by vortex. Red blood cell lysis was allowed to occur for 12 minutes, after which, 9 mL of flow cytometry staining buffer (eBioscience) was added to the sample to stop the lysis reaction. Samples were then centrifuged at 500× g at room temperature for 5 minutes. The supernatant was discarded, and the cell pellet was resuspended by vortexing. To wash the sample, another 9 mL of flow cytometry staining buffer was added and then the supernatant was discarded after 5 further minutes of centrifugation at 500× g. The remaining fluorescently labeled white blood cell samples were redispersed by pipette and vortex and used for experiments. For imaging, 10 µl of sample were placed onto a well-cleaned microscope slide and covered with a No. 2 coverslip (0.17 to 0.25 mm thickness).

To evaluate the HOIM signal from each white blood cell subtype, lymphocytes, monocytes, and granulocytes were separated into distinct samples using a cell sorter and then imaged. Processed CD-Chex samples were pre-filtered using a 5 mL Falcon tube cell strainer to remove cell clumps, then loaded into a FACSAria cell sorter (Becton Dickinson) for sorting into separate tubes. Manual gates were drawn around lymphocyte, monocyte, and granulocyte populations in the cell sorter software on two dimensional plots of forward scatter area versus side scatter area after initially running the sample. These gates were used as the input to the cell sorter to physically separate the three white blood cell groups into three tubes blocked with a 5% w/w BSA PBS solution. Sorted samples were also re-run through the sorter for a purity check. At the conclusion of sorting, the separate lymphocyte, monocyte, and granulocyte samples were centrifuged at 500× g for 5 minutes, the supernatant was discarded, and the samples were imaged. Five fields of view for each sample were acquired, and analyzed.

Figure 3A:
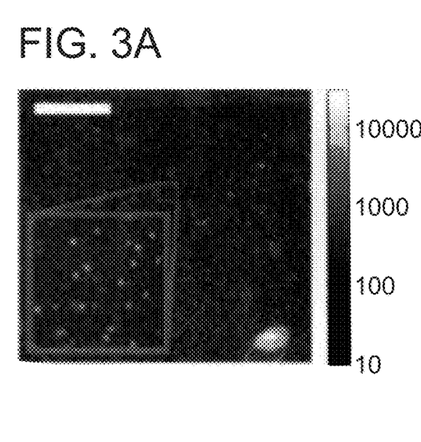
FIGS. 3a, 3c, and 3e are 4× HOIM images of lymphocytes, monocytes and granulocytes, respectively.
Figure 3B:
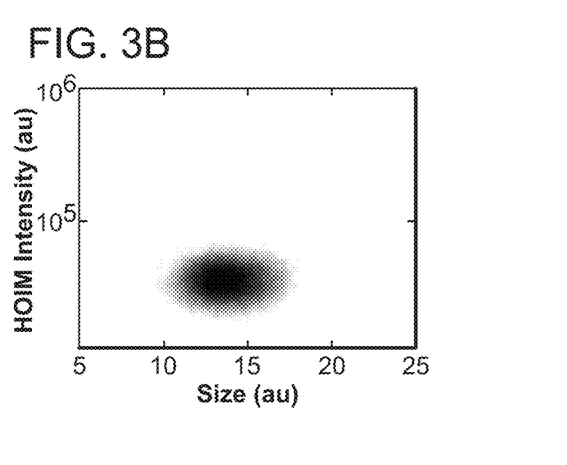
FIGS. 3b, 3d, and 3f are graphs of HOIM intensity against size and plotted as density plots.
Figure 3C:
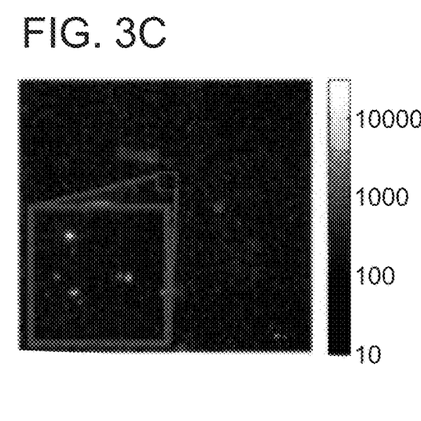
Figure 3D:
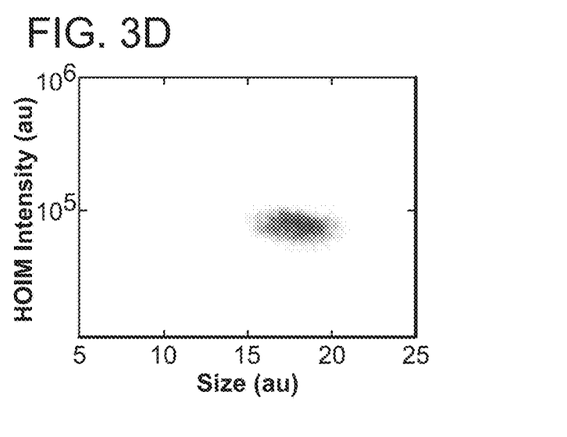
Figure 3E:
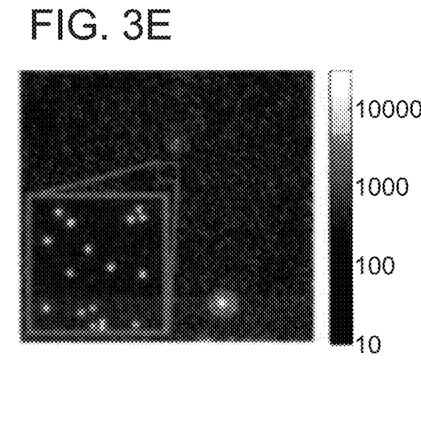
Figure 3F:
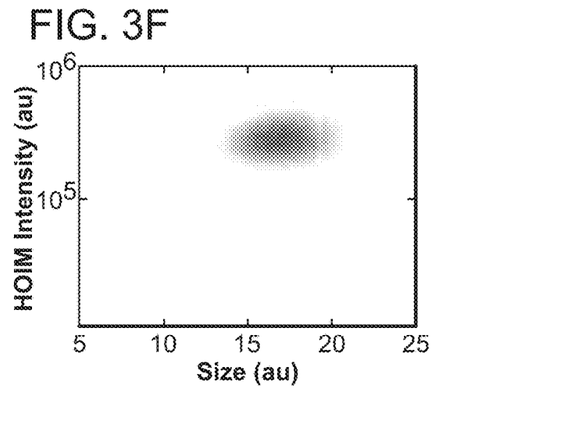

Example HOIM images of each cell displayed on a log color scale (FIG. 3a,c,e) demonstrate slight qualitative differences in signal intensity between lymphocytes, monocytes, and granulocytes. Insets with colored borders represent digitally zoomed, in areas of interest for each image displaying each cell type under HOIM. Using the automated algorithm described above, the size of each cell in the image as well as integrated signal intensity are calculated, to place each cell event into a two dimensional density dot plot where the intensity of the color correlates to the density of data points in that region (FIG. 3b,d,f). Density plot data is accumulated from five separate fields of view for each sample. These two dimensional density dot plots are standard in flow cytometry to assess clustering of various cell populations using any two measured parameters, From the size versus HOIM signal intensity plots (FIG. 3b,d,f) it is clear that each particular white blood cell type fells into a distinct region of the two dimensional data space. In addition to the three primary cell groups, lower HOIM signal intensity (<104) cellular debris is present in all the sorted samples (data not shown). These debris data points are easily removed from the analysis using CD45 gating.

Figure 4A:
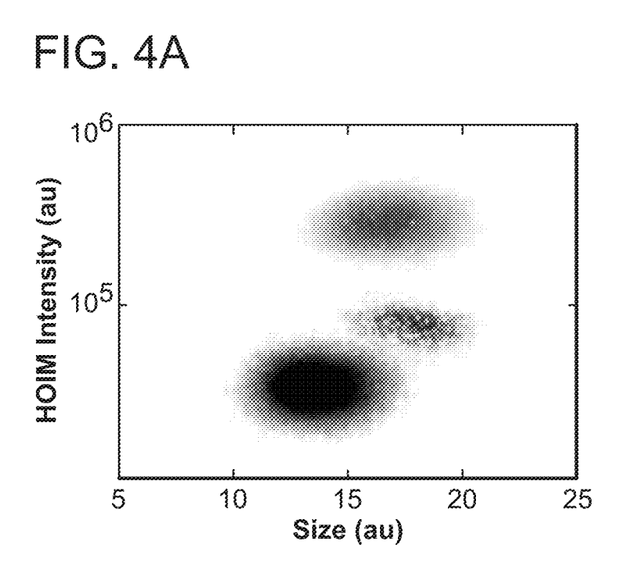
FIG. 4a is a graph of HOIM intensity against size for control samples sorted into three leucocyte groups.

Combining the size and HOIM intensity data from the three white blood cell groups into one density plot (FIG. 4a) demonstrates for this particular sample the data-space separation of the lymphocyte, monocyte, and granulocyte populations. Flow cytometry data from the same sorted cell samples (FIG. 4b) shows similar patterns of clustering for the three cell groups when the forward scatter and side scatter data are plotted. This demonstrates that tor white blood cell analysis, size and intensity as quantified from HOIM images can serve as a surrogate for scatter measurements in flow cytometry, and potentially allow for the separation of the three white blood cell groups without the need of multiple fluorescence channels to identify specific cellular populations. This could lead to the use of HOIM as a surrogate for forward and side scatter in microscopy-based cytometry of stationary planar samples.

Figure 4B:
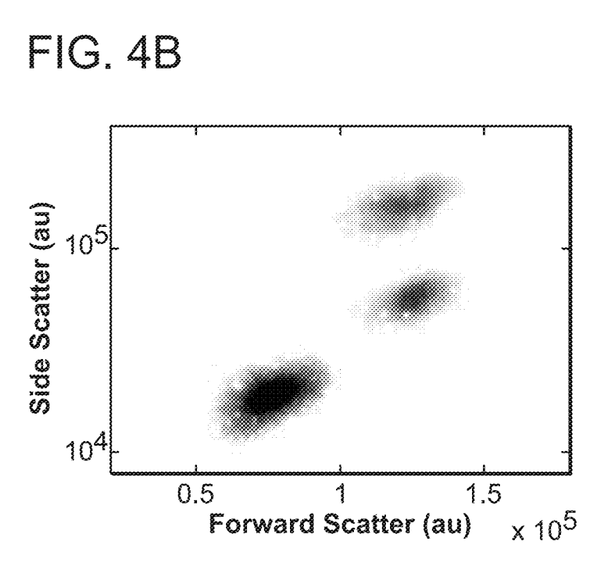
FIG. 4b is a graph of side scatter versus forward scatter in flow cytometry data for CD-Chex samples after sorting.
Figure 5A:
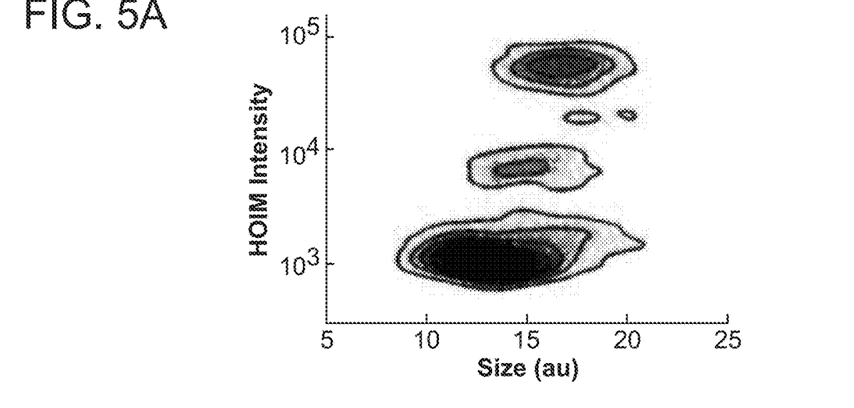
FIG. 5a is a graph of HOIM intensity against size as quantified from one unsorted CD-Chex sample showing regions associated with red blood cells and debris, lymphocytes, monocytes and granulocytes.
Figure 5B:
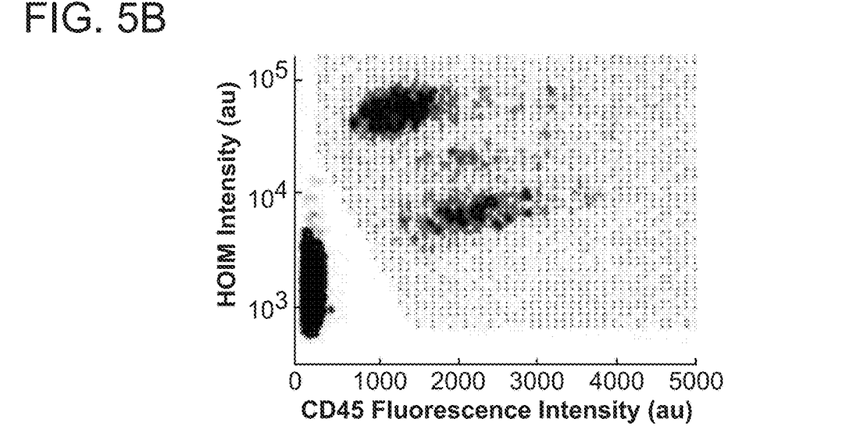
FIG. 5b is a graph of HOIM intensity against CD45 florescence intensity showing separation of white blood cell groups from debris.

While sorting the cell samples senses as a well-validated control method for assessing HOIM measurements as a surrogate for forward and side scatter, sorted samples do not represent realistic input samples to a flow cytometry analyzer in a clinical or research setting. Therefore, processed but unsorted CD-Chex samples were imaged using HOIM and fluorescence. Density dot plot and overlaying contour data of size versus HOIM intensity as quantified by the automated analysis routine shows four distinguishable clusters (FIG. 5a). Lymphocyte, monocyte, and granulocyte populations are still present, similar to the sorted sample data in FIG. 4, plus the inclusion of remaining red blood cell and other cell debris which possess on average smaller size and lower HOIM intensity than the lymphocyte group. To accurately identify and remove debris from further analysis, the CD45 fluorescence image was analyzed using the event detection locations front the accompanying HOIM image. Substituting HOIM size (i.e. forward scatter) with the CD45 fluorescence intensity in the two dimensional density dot plot distinctly shows the debris field as low fluorescence intensity, while white blood cells possess high fluorescence intensity (FIG. 5b). The red patterned region in FIG. 5b indicates the manually determined CD45 gate that removes all non-white blood cells from further analysis. Applying the gated region in FIG. 5b to the data in FIG. 5a results in a size and HOIM density plot with overlaying contours that distinctly shows three groups of cell populations within the unsorted samples, each of which overlaps with a distinct region in 2D space similar to the sorted data in FIG. 4a. This data visually suggests that HOIM imaging can distinguish the three primary cell group clusters from an unsorted white blood cell sample, similar to flow cytometry scatter measurements (FIG. 4b). It is important to note that CD45 is commonly used in flow cytometry analysis of white blood cell populations, particularly when gating for lymphocytes [23]. CD45 is used to rule out debris and better separate cell clusters when forward and side scatter alone are insufficient for a particular sample. We have used CD45 as a control measurement to remove debris from our analysis. The majority of the analyzed samples could have been further analyzed without the need for CD45 gating.

Figure 5C:
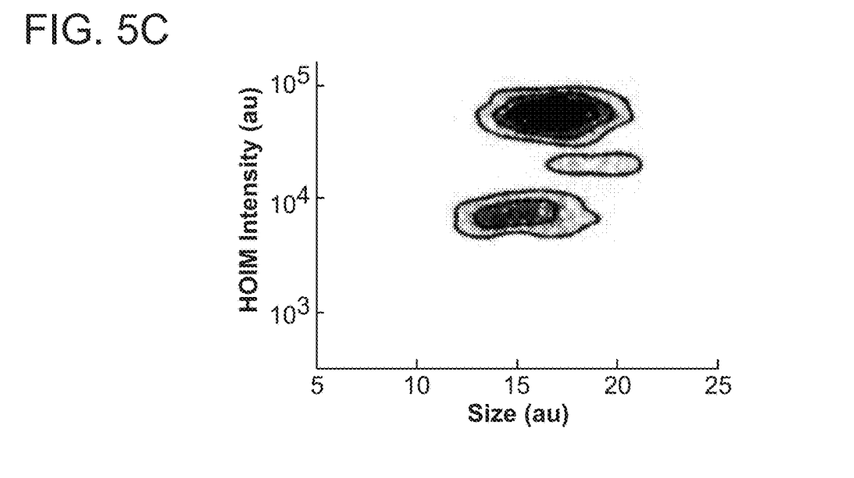
FIG. 5c is a graph of HOIM intensity against size revealing three distinct groups in an unsorted sample corresponding to lymphocytes, monocytes and granulocytes.

To assess the relative number of lymphocytes, monocytes, and granulocytes in the unsorted sample, three individual observers were asked to manually gate the CD-45-gated size versus HOIM density dot plots with overlying contours (FIG. 5c) into three population clusters. Manual gating was performed for data from each field-of-view for each sample using a custom Matlab graphical user interface. To mitigate any observer bias, data from a set of images were separated, from the testing set and used for training of each individual. The observers were also allowed to see the sorted sample data (FIG. 4) to understand the relative position of white blood cell types in two dimensional space. Once the individual felt comfortable placing manual gates on the training set, they drew manual gates on the separate test data only once, in random order of sample number and field-of-view, blinded from the results. Once complete, the results from the three observers were compiled, averaged, and compared across samples. For the testing set, data from 6 fields of view for each sample were analyzed. Inter-observer variance for each manually drawn gate was less than 5% in 97% of the gates drawn.

Figure 6A:
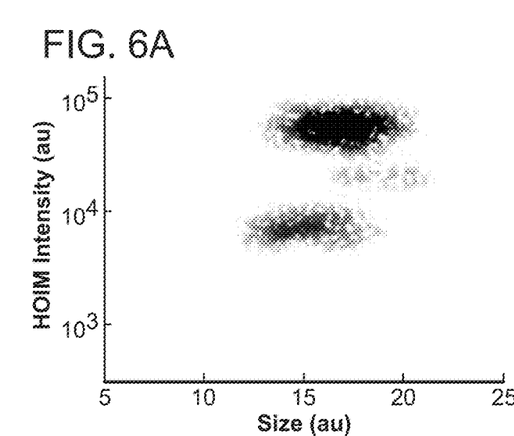
FIG. 6a is a graph of HOIM intensity against size as quantified from one unsorted CD-Chex sample after florescence gating.
Figure 6B:
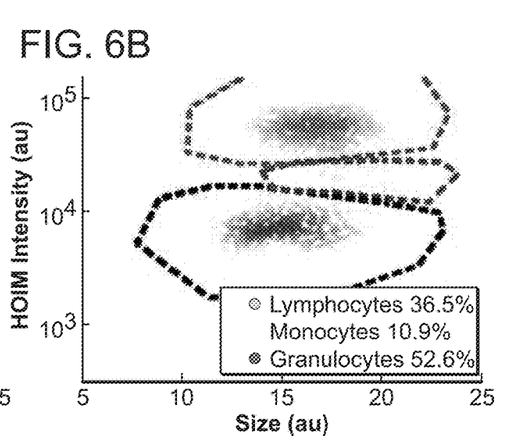
FIG. 6b is a graph of HOIM intensity against size after manual gating into three clusters.
Figure 6C:
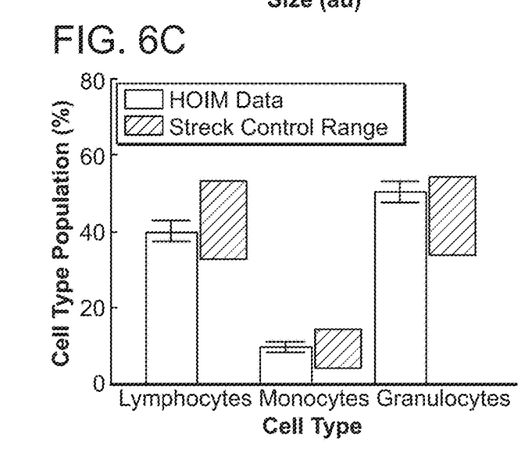
FIG. 6c is a graph of cell type population against cell type showing mean cell group clustering values that fall within the control range supplied by the CD-Chex manufacturer.

A density dot plot is shown for one particular field-of-view for one CD-Chex sample (FIG. 6a), as well as the matching data after each point has been manually clustered into a lymphocyte (blue), monocyte (green), or granulocyte (orange) cluster population (FIG. 6b). Manually drawn gates from one individual observer are represented by colored lines. For the data points from one field-of-view and one observer in FIG. 6b, the calculated relative white blood cell population percentages of lymphocytes, monocytes, and granulocytes in fee sample are 36.5%, 10.9%, and 52.6%, respectively. After averaging outputs from three observers, mean population percentages for six fields of view for the sample are 40.0±2.8% for lymphocytes, 9.7±0.9% for monocytes, and 50.3±2.2% for granulocytes (FIG. 6c). Importantly, the manufacturer of the CD-Chex samples supplies mean and range values for the sample, and states that for any given flow cytometer, the means from multiple runs should fall within 33% and 53% for lymphocytes, 4.3% and 14.3% for monocytes, and 34.1% and 54.1% for granulocytes (red, FIG. 6c). The mean cell population values for this sample found through automated image processing and manual clustering of HOIM images fall within the appropriate ranges for the three major white blood cell groups (FIG. 6c).

Figure 6D:
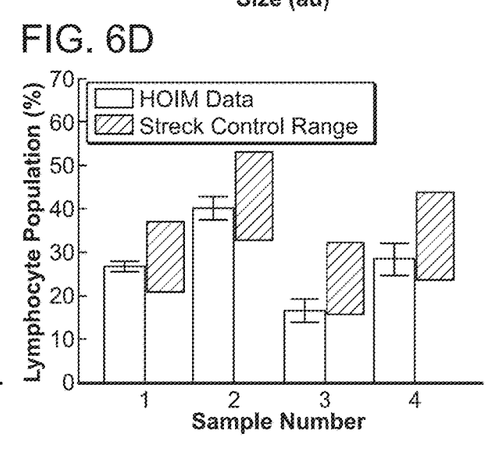
FIG. 6d is a graph of lymphocyte population against sample number showing that the HOIM approximations for lymphocyte population ratios fall within the range supplied by the CD-Chex manufacturer.

To assess the accuracy of HOIM measurements across varying samples, four CD-chex samples of varying lymphocyte population ratios were processed, imaged using HOIM and fluorescence, and manually gated by three observers. HOIM with CD45 gating was able to differentiate between blood samples with varying cell population ratios. For four samples, the lymphocyte population percentages for each sample are plotted in FIG. 6d as well as the reported ranges from the sample manufacturer (red, FIG. 6d). Each of the means falls within the range reported by the manufacturer. The mean lymphocyte population percentage as calculated by HOIM and manual clustering scales with the reported mean supplied by the manufacturer with a correlation coefficient of 0.98. This data suggests that HOIM imaging and the accompanying algorithms to estimate size and signal intensity can classify the percentage of each white blood cell group, similar to forward and side scatter in flow cytometry. Additionally, without optimizing the concentration of cells to maximize foe number of cells in one field-of-view, the number of white blood cells in a single field-of-view ranged from 965 to 4,296.

In this document, we have presented the use of a highly oblique illumination strategy and image processing algorithm for differentiating cell subtypes using scatter parameters, similar to flow cytometry. The incorporation of an elegant modular highly oblique illuminator alongside a commercial microscope allowed for differentiation of white blood cell types without the need for high resolution spatial morphology or labeling. In both sorted and unsorted blood cell samples, white blood cell subtypes were differentiable based on size and HOIM signal intensity as analyzed by an automated image processing algorithm. In addition, samples analysed by HOIM imaging and automated image processing followed by manual gating resulted in three part white blood cell differentials that fell within the control values supplied by the sample manufacturer.

Using HOIM to measure direct surrogates of forward and side scatter could allow for experiments to move well beyond a basic three part white blood cell differential that can be achieved with a common cell analyzer into more versatile and complex cytometry applications. In previous literature, variants of dark field microscopy have been used for label-free distinction of cell types in a number of applications using automated image processing [24-27], but existing techniques either do not supply direct correlates of forward and side scatter measurements, require high magnification spatial morphology to classify cell types, or create a cell-specific image processing classifier that is not broadly applicable to a range of applications or cell types. The no age analysis methods demonstrated here have the potential to move beyond basic white blood cell differentials, and are translatable to fluorescence images as well [19, 20]. Additionally, although the illuminator supplies a version of dark field contrast (a ubiquitous and well established technology), and oblique illumination techniques have previously been employed for a number of applications [15, 28-32], the HOIM illuminator was purposefully designed to allow for accurate surrogate measurements of forward and side scatter using microscopy, something not previously demonstrated in the literature. The illuminator was designed for homogeneous illumination over a wide field of view, to operate alongside low working distance objectives, and to mimic side scatter measurements of flow cytometry by encompassing a specific range of collection angles that relate to internal cell complexity [6] and allow for significant separation of cell types [16]. Acquiring forward and side scatter surrogate measures that allow for direct comparison to the wealth of existing flow cytometry data [7], this illumination and image analysis method can move well beyond the applications shown in this work.

Some considerations must be made when implementing HOIM on existing fluorescence microscopes. First, although studies have demonstrated that the intensity of low angle forward scattered light varies with particle volume [8], it is important to note that size is not monotonically linearly correlated with forward scatter [7]. Forward scatter is affected by biological parameters including size and refractive index mismatch with surrounding media [33], and instrumentation parameters such as wavelength of illumination and precise range of angles collected [7, 34]. Therefore, although size has been shown to be a reasonable surrogate for forward scatter in differentiating white blood cell types here, that does not imply that the relationship will hold true for all samples. A benefit of accurate Gaussian fitting in the algorithm described here is there are a number of size and shape metrics that can be used to describe the cell in place of area including minimum dimension length, maximum dimension length, eccentricity, etc.

Another consideration is illumination homogeneity. To accurately quantify cell signal brightness and distinguish between cell groups, homogeneous illumination is essential throughout the field-of-view. Using a highly oblique method as described here allows for homogeneous wide field of view illumination. To assess illumination homogeneity for this application, a field-of-view of sorted lymphocytes (i.e., the lowest scattering cell group) and then granulocytes (i.e., the highest scattering cell group) were each split into 25 equal spatial quadrants and analyzed using the algorithm presented here to assess each cell's brightness. The standard deviation of cell brightness in each quadrant was at minimum greater than twice the standard deviation of the mean of the 25 quadrants for both cell types. This indicates that any variations in illumination across the field-of-view were smaller than natural variations in cell scatter and that illumination homogeneity was not a confounding factor. Additionally, although the HOIM signal magnitude can be used to differentiate cell types, scatter-based imaging is not specific to cells. Dirt and scratches on the specimen container (e.g., microscope slide or petri dish) will be visible in the field-of-view. This implies that thorough cleaning of the specimen container is important to avoid background signal.

For these studies, microscope slides and coverslips were alternatingly rinsed with deionized water and then ethanol twice, then dried with compressed air. To further control for distinguishing from contaminants in our studies, CD45 was used to isolate white blood cells from other features in the scatter-based images. For most of the samples, we observed that contaminants had lower HOIM signal intensity and smaller size than the white blood cells, and could often be segmented out without the need for CD45. Last, stray light can induce large background HOIM signals that can saturate the detector. Sources of this stray light can include surfaces on the specimen stage, optical components opposite from the detection objective (e.g., transmission condenser), and reflections from the microscope objective surfaces, among others. To avoid the detection of stray light, the outside surfaces of the microscope objective and the specimen stage were covered with blackout tape (AT205, Thorlabs).

The characterization of cells in the research setting is often divided into two protocols; the analysis of small cell numbers using high resolution microscopy and high throughput population level analysis using flow cytometry or high content analyzers. Cellular astronomy allows researchers access to population level datasets similar to flow cytometry using their existing fluorescence microscopy infrastructure and without the need for purchasing additional dedicated instruments. This greatly enhances the versatility of fluorescence microscopes, and could potentially allow researchers to acquire cytometry data with their existing microscopes and without the need to purchase dedicated flow cytometers, effectively increasing access to cytometry measurements in life science research. Despite the slower cell throughout of our system in comparison to traditional flow cytometry, it is important to note that the field-of-view size, illumination and detection scheme were designed to detect a statistically significant number of events (100 s to 1000 s) for a number of applications from a single field-of-view. Additionally, this method could be used in concert with high resolution microscopy, as a function of time, or in an adherent cell's native in vitro environment while avoiding potentially destructive or epitope-altering cell recovery methods [35].

The use of HOIM could also be beneficial for those developing cellular astronomy for clinical cytometry applications including immunophenotyping. Although low resolution fluorescence microscopy is not a new idea in the context of cell astronomy, we are the first to demonstrate the ability to collect and analyze elastic scatter surrogates of flow cytometry for hundreds to thousands of individual cells simultaneously over a wide field-of-view using an elegant oblique illumination scheme. Effectively, this work presents the first successful use of wide field-of-view microscopy to gather analogs to the forward and side scatter measurements of flow cytometry. The ability to distinguish cell subtypes using scatter parameters is essential for minimizing use of the optical wavelength spectrum bandwidth that otherwise is necessary for further cellular subtyping with fluorescent labels (e.g., CD45, CD3, etc.). The addition of label free cell population subtyping using HOIM could aid in the adoption of cellular astronomy as a viable cytometry option for life science researchers, and aid in further translation to clinical uses.

The technology disclosed herein provides an elegant solution for quantitative wide angle scatter imaging and a surrogate measure of forward scatter for cells over a wide field of view using low magnification optics, where spatial morphology is essentially lost. In one specific application, this technology can distinguish between white blood cell subtypes without the need for stains or dyes. Although the major white blood cell groups can be differentiated at high magnification using spatial morphology and advanced image processing, throughput is very limited to small fields of view (100's of micrometers in each dimension) due to the high resolution requirements to characterize spatial morphology. Flow cytometers characterize white blood cells without the need for high resolution images by assessing how light scatters in the forward and side direction when interacting with individual flowing cells. Our technology translates this idea to planar imaging cytometry so that cells can be classified over wide fields of view (multiple millimeters in each dimension) using standard low magnification/low numerical aperture detection optics. This allows successful grouping of cells without the need for high resolution spatial morphology and thus much larger fields of view and increased throughput. In addition, imaging non-flowing samples allows microscopy to revisit the same cell for further analysis, something that flow cytometry does not allow for.

Although oblique illumination has been used for darkfield microscopy, it has never been used for quantitative side scatter imaging, especially at low resolution/wide field of view, where throughput would be the greatest and where spatial morphology is essentially lost. In addition, the incorporation of advanced quantification methods into this precise application of forward and side scatter surrogate measurements is not an obvious one. Finally, for the past few decades, a number of companies have developed imaging technologies for cellular analysis, or imaging based cytometry. However, to this date, no planar cellular imaging cytometry device on the market has managed to develop accurate side scatter technologies for their device, rendering most of these devices limited to a research setting. Given the long history of these devices, and the longstanding requirement of forward and side scatter to differentiate white blood cell groups when spatial morphology is lost, it is clearly not an obvious combination of technologies.

This technology is especially advantageous for certain clinical applications of cellular characterization that require high throughput and cell grouping without the use of fluorophores. For example, others have proposed the use of planar imaging cytometry as a cost effective alternative to clinical flow cytometry in characterization of blood samples. However, proper clinical cytometry of blood samples requires identification of white blood cell groups into three primary subclasses (lymphocytes, monocytes, and granulocytes) prior to characterization of fluorescent biomarkers. The technology disclosed herein addresses the need of white blood cell scatter-based grouping for clinical cytometry applications.

To date there have been no demonstrations of quantitative side scatter imaging to characterize cells in the low resolution regime where spatial morphology is essentially lost. At high resolution, and with the assistance of staining protocols, cells (particularly white blood cells) can be automatically identified with advanced image processing algorithms using spatial morphology and sub-cellular feature extraction. However, throughput at high resolution is significantly limited. Using our technology, cells can be characterised over a much larger field of view (and with increased throughput) without the need for stains, dyes, or other contrast agents. For one particular application, we can separate white blood cell groups over multiple millimeter dimension fields of view.

The technology described here effectively supplies wide angle near-orthogonal scatter information, which correlates with internal cellular complexity of cells, and can be used to distinguish cell types without the need for high resolution features, in a label-free manner. Wide angle scattering can also be achieved using standard darkfield microscopy using any of the embodiments of a darkfield illuminator (Abbe, parabloid, cardioid, catoptric, dioptric, catadioptric, etc.). However, these illuminators can only supply homogenous illumination for wide angle scatter over small fields of view, and are often limited to high magnification detection optics, which ultimately limits their clinical utility for high cell throughput applications. At low resolution and wide field of view, darkfield microscopy can be achieved over the field of view, but not for wide angle scattering events. In transmission darkfield imaging, the dark field cone over wide fields of view will often come very close to intersecting the detection optics, so wide angle scattering is mixed with low angle scattering. In reflection darkfield imaging, the signal recovered by the objective is not wide angle scatter, but backscatter, a signal that does not correlate to cellular complexity in the same manner as wide angle (close to orthogonal) scattering. Darkfield condensers are also much more cumbersome when setting up and aligning for homogenous illumination required for quantitative imaging over the large field of view. The technology described here supplies quantitative wide-angle scatter information within the same cone of angles as flow cytometry over a wide field of view, with high homogeneity of illumination, and in a manner that is simple to setup, align, and maintain, enabling cellular samples to be analyzed quickly (cell throughput), easily (instrumentation setup), and in a clinically-relevant manner (flow cytometry). In addition, givers similar cost and system complexity constraints, the illumination system described here should achieve greater homogeneity over larger fields of view.

In addition, the use of size and side scatter signal intensity values for each cell in the image space is a definitive method to group cell types similar to flow cytometry.

In addition to white blood cell grouping, this analysis could be used to distinguish a range of cell types and subtypes including red blood cells, platelets, gametocytes (malaria) fibroblasts, epithelial cells, endothelial cells, cancer cells, any type of immune cell or precursor immune cell, stem cells and their precursors, etc., and could be used for microvesicles, exosomes, etc.

This technology works with any cellular suspension dispersed in a planar geometry. This includes cell suspensions that are wet mounted onto a microscope slide with a coverglass, smeared cell samples without a coverglass, or cells dispersed onto any substrate including microscope slides, coverglass, petri dishes.

The numbers in square brackets refer to the references listed herein. The contents of all of these references are incorporated herein by reference in their entirety.

It is recognized that modifications and variations of the invention disclosed herein, may be apparent to those of ordinary skill in the arts and it is intended that all such modifications and variations be included within the scope of the appended claims.

REFERENCES

1. H. M. Shapiro, ""Cellular astronomy"—a foreseeable future in cytometry," Cytometry. Part A: the journal of the International Society for Analytical Cytology 60, 115-124 (2004).
2. H. M. Shapiro, "The Cytometric Future: It Ain't Necessarily Flow!," Flow Cytometry Protocols, Third Edition 699, 471-482 (2011).
3. H. M. Shapiro and N. G. Perlmutter, "Personal cytometers: Slow flow or no flow?," Cytom Part A 69A 620-630 (2006).
4. H. M. Shapiro and N. G. Perlmutter, "Killer applications: Toward affordable rapid cell-based diagnostics for malarta and tuberculosis," Cytom Part B-Clin Cy 74B, S152-S164 (2008).
5. K. D. Wittrup, R. J. Westerman, and R. Desai, "Fluorescence Array Detector for Large-Field Quantitative Fluorescence Cytometry," Cytometry 16, 206-213 (1994).
6. W. P. Hansen, R. A. Hoffman, S. H. Ip, and K. W. Healey, "Light scatter as an adjunct to cellular immunofluorescence in flow cytometric systems," Journal of clinical immunology 2, 32S-41S (1982).
7. H. M. Shapiro, *Practical flow cytometry*, 4th ed. (Wiley-Liss, New York, 2003), pp. 1, 681
8. P. F. Mullaney, M. A. Vandilla, J. R. Coulter, and P. N. Dean, "Cell Sizing—a Light Scattering Photometer for Rapid Volume Determination," Rev Sci Instrum 40, 1029-& (1969).
9. G. C. Salzman, J. M. Crowell, J. C. Martin, T. T. Trujillo, A. Romero, P. F. Mullaney, and P. M. Labauve, "Cell Classification by Laser Light-Scattering—Identification and Separation of Unstained Leukocytes," Acta Cytol 19, 374-377 (1975).
10. B. J. Price, V. H. Kollman, and G. C. Salzman, "Light-Scatter Analysis of Microalgae—Correlation of Scatter Patterns from Pure and Mixed Asynchronous Cultures," Biophysical journal 22, 29-36 (1978).
11. L. A, Sklar, Z. G. Oades, and. D. A. Finney, "Neutrophil degranulation detected by right angle light scattering: spectroscopic methods suitable for simultaneous analyses of degranulation or shape change, elastase release, and cell aggregation," Journal of immunology 133, 1483-1487 (1984).
12. P. L. Mcneil, A. L. Kennedy, A. S. Waggoner, D. L. Taylor, and R. F. Murphy, "Light-Scattering Changes during Chemotactic Stimulation of Human-Neutrophils—Kinetics Followed by Flow-Cytometry," Cytometry 6, 7-12 (1985).
13. M. L. Benson, D. C. Mcdougal, and D. S. Coffey, "The Application of Perpendicular and Forward Light Scatter to Assess Nuclear and Cellular Morphology," Cytometry 5, 515-522 (1984).
14. L. E. Mcgann, M. L. Walterson, and L. M. Hogg, "Light-Scattering and Cell Volumes in Osmotically Stressed and Frozen-Thawed Cells," Cytometry 9, 33-38 (1988).
15. J. Yguerabide and E. E. Yguerabide, "Light-scattering submicroscopic particles as highly fluorescent analogs and their use as tracer labels in clinical and biological applications," Analytical biochemistry 262, 157-176 (1998).
16. D. Watson, N. Hagen, J. Diver, P. Marchand, and M. Chachisvilis, "Elastic light scattering from single cells: orientational dynamics in optical trap," Biophysical journal 87, 1298-1306 (2004).
17. I. Smal, M. Loog, W. Niessen, and E. Meijering, "Quantitative comparison of spot detection methods in fluorescence microscopy," IEEE transactions on medical imaging 29, 282-301 (2010).
18. A. D. Herbert, A. M. Carr, and E. Hoffmann, "FindFoci: a focus detection algorithm with automated parameter training that closely matches human assignments, reduces human inconsistencies and increases speed of analysis," PloS one 9, e114749 (2014).
19. G. Gonzalez, Madrid-MIT M+Visión Consortium, Massachusetts Institute of Technology, 77 Massachusetts Ave, Cambridge, Mass. 02139, and S. Dave, J. M. Tucker-Schwartz, E. Pardo, N. Malpica are preparing a manuscrip to be called "Towards Quantitative Cellular Astronomy."
20. E. Pardo, Medical Image Analysis and Biometry Lab, Universidad Rey Juan Carlos, Móstoles, Madrid, Spain and G. Gomalez, J. M. Tucker-Schwartz, S. Dave, N. Malpica are preparing a manuscript to be called "Quantitative Cell Analysis Pipeline for Cellular Astronomy."
21. J. Cunliffe, N. Derbyshire, S. Keeler, and R. Coldwell, "An approach to the validation of flow cytometry methods," Pharmaceutical research 26, 2551-2557 (2009).
22. M. A. Owens, H. G. Vail, A. A. Hurley, and S. B. Wormsley, "Validation and qualify control of immunophenotyping in clinical flow cytometry," J Immunol Methods 243, 33-50 (2000).
23. J. K. A. Nicholson, M. Hubbard, and B. M. Jones, "Use of CD45 fluorescence and side-scatter characteristics for gating lymphocytes when using the whole blood lysis procedure and flow cytometry," Cytometry 26, 16-21 (1996).
24. N. Wei, E. Flaschel, K Friehs, and T. W. Nattkemper, "A machine vision system for automated non-invasive assessment of cell viability via dark field microscopy, wavelet feature selection and classification," BMC bioinformatics 9, 449 (2008).
25. A. Ciurte, T. Marita, and R. Buiga, "Circulating tumor cells classification and characterization in dark field microscopic images of unstained blood," in 2015 *IEEE International Conference on Intelligent Computer Communication and Processing (ICCP)*, (IEEE, Cluj-Napoca, 2015).
26. N. Wei, J. You, K. Friehs, E. Flaschel, and T. W. Nattkemper, "An in situ probe for on-line monitoring of cell density and viability on the basis of dark field microscopy in conjunction with image processing and supervising machine learning," Biotechnol Bioeng 97, 1489-1500 (2007).
27. K. Reeve, J. Arellano, T. Gruner, W. Reilly, B. Smith, and S. Zhou, "A comparison of differential leucocyte counts measured by conventional automated venous haematology and darkfield microscopic examination of fresh capillary blood," Advances in Integrative medicine 2, 125-129 (2015).
28. L. J. Johnson, D. F. Hanley, and N. V. Thakor, "Optical light scatter imaging of cellular and sub-cellular morphology changes in stressed rat hippocampal slices," J Neurosci Meth 98, 21-31 (2000).
29. S. Landry, L. H. DeGagne, P. L. McGhee, and W. J. Keeler, "Oblique incidence reflection imaging of live cells: improving contrast and image quality with an objective mask," J. Microsc-Oxford 227, 185-189 (2007).
30. S. Landry, P. L. McGhee, R. J. Girardin, and W. J. Keeler, "Monitoring live cell viability: Comparative study of fluorescence, oblique incidence reflection and phase contrast microscopy imaging techniques," Optics express 12, 5754-5759 (2004).
31. Y. Kawano, C. Higgins, Y. Yamamoto, J. Nyhus, A. Bernard, H. W. Dong, H. J. Karten, and T. Schilling, "Darkfield Adapter for Whole Slide Imaging: Adapting a Darkfield Internal Reflection Illumination System to Extend WSI Applications," PloS one 8 (2013).
32. J. Yguerabide and E. E. Yguerabide, "Resonance light scattering particles as ultrasensitive labels for detection of analytes in a wide range of applications," J Cell Biochem 84, 71-81 (2001).
33. T. K. Sharpless, M. Bartholdi, and M. R. Melamed, "Size and Refractive-Index Dependence of Simple Forward Angle Scattering Measurements in a Flow System Using Sharply-Focused Illumination," J Histochem Cytochem 25, 845-856 (1977).
34. G. C. Salzman, "Light scatter: detection and usage," Current protocols in cytometry/editorial board, J. Paul Robinson, managing editor . . . [et al.] Chapter 1, Unit 1 13 (2001).
35. A. Bundscherer, M. Malsy, R. Lange, P. Hofmann, T. Metterlein, B. M. Graf, and M. Gruber, "Cell harvesting method influences results of apoptosis analysis by annexin V staining," Anticancer research 33, 3201-3204 (2013).

What is claimed is:
1. System for scatter-based differentiation of cells comprising:
a planar substrate having cells disposed thereon for imaging;

a microscope employing relatively low magnification detection optics providing a wide field of view focused on the cells on the substrate and defining a microscope optical axis;

an illuminator for delivering light to the cells on the substrate focused to a spot larger than the field of view of the microscope, the illuminator having an illumination optical axis highly oblique to the microscope optical axis, wherein scattered light is collected by the microscope; and a detection system receiving the scattered light from the microscope to provide a measure of signal intensity and a measure of size for each cell for discrimination of cell type.

2. The system of claim 1 wherein the cells are white blood cells.

3. The system of claim 1 wherein the cells are red blood cells.

4. The system of claim 1 wherein the cells are cancerous cells.

5. The system of claim 1 wherein the cells are stem cells.

6. The system of claim 1 wherein the cells are epithelial cells.

7. The system of claim 1 wherein the cells are nerve cells.

8. The system of claim 1 wherein the cells are hepatocytes.

9. The system of claim 1 wherein the cells are adipocytes.

10. The system of claim 1 wherein the cells are fibroblasts.

11. The system of claim 1 wherein the cells are muscle cells.

12. The system of claim 1 wherein the low magnification, is between 0.5× to 4×.

13. The system of claim 1 wherein the smallest dimension of the field of view is anywhere from 1 mm to 30 mm.

14. The system of claim 1 wherein the illuminator includes a light emitting diode with center wavelength ranging anywhere from 350 nm to 700 nm.

15. The system of claim 1 wherein the highly oblique angle is at least 50 degrees.

16. The system of claim 15 wherein the oblique angle is approximately 82 degrees.

17. The system of claim 1 wherein the detection system includes a planar optical detector of any rectangular dimensions including a semiconductor charge-coupled device (CCD) or active pixel sensor array in complementary metal-oxide-semiconductor (CMOS) or N-type metal-oxide semiconductor (NMOS).

18. The system of claim 1 wherein the detection system includes algorithms to generate approximate size and signal intensity from each cell.

19. The system of claim 18 wherein the fits of the detected events is determined by a statistical approach involving fitting to the image a mixture model composed of at least a distribution representing the background and a distribution representing at least one event.

20. The system of claim 18 where the background distribution is a uniform probability density function.

21. The system of claim 18 where the event distribution is a Gaussian probability density function.

22. The system of claim 18 where the fitting method is the Expectation-Maximization algorithm.

* * * * *